United States Patent [19]

Ellison et al.

[11] 4,382,130
[45] May 3, 1983

[54] MOISTURE CURABLE COMPOSITIONS AND ARYLOXYPHOSPHONIUM SALTS

[75] Inventors: Robert H. Ellison, Schenectady; Martin A. Byrne, Troy, both of N.Y.

[73] Assignee: General Electric Company, Schenectady, N.Y.

[21] Appl. No.: 311,126

[22] Filed: Oct. 14, 1981

Related U.S. Application Data

[63] Continuation of Ser. No. 143,821, Apr. 25, 1980, Pat. No. 4,341,714.

[51] Int. Cl.³ .............. C08G 59/68; C08G 8/10; C08F 4/72; C08F 4/00
[52] U.S. Cl. .............. 525/337; 525/340; 525/506; 525/507; 526/192; 526/193; 528/13; 528/19; 528/23; 528/89; 528/138; 528/139; 528/141; 528/236; 528/240; 528/242; 528/313; 528/356; 528/408; 528/409; 528/423; 528/424
[58] Field of Search .............. 528/13, 19, 23, 89, 528/138, 139, 141, 236, 240, 242, 313, 356, 408, 409, 423, 424; 526/192, 193; 525/340, 337, 506, 507

[56] References Cited

U.S. PATENT DOCUMENTS

| | | | |
|---|---|---|---|
| 4,000,115 | 12/1976 | Jacobs | 528/89 |
| 4,069,055 | 1/1978 | Crivello | 528/408 X |
| 4,302,574 | 11/1981 | Doorakian et al. | 528/89 |

OTHER PUBLICATIONS

Rydon et al., "Organic Chemistry of Phosphorus", Chemical Abstracts 51, 3487e (1957).

*Primary Examiner*—Earl A. Nielsen
*Attorney, Agent, or Firm*—William A. Teoli; James C. Davis, Jr.; James Magee, Jr.

[57] ABSTRACT

Certain aryloxyphosphonium salts have been found to be effective as curing agents for various cationically polymerizable organic materials, such as epoxy resins, when incorporated into such materials. The materials are found to be moisture curable coating compositions.

7 Claims, No Drawings

MOISTURE CURABLE COMPOSITIONS AND ARYLOXYPHOSPHONIUM SALTS

This application is a division of application Ser. No. 143,821, filed Apr. 25, 1980 now U.S. Pat. No. 4,341,714, issued July 27, 1982.

CROSS REFERENCE TO RELATED APPLICATION

Reference is made to copending application of James V. Crivello, Ser. No. 949,642, filed Oct. 10, 1978 now U.S. Pat. No. 4,219,654 for Photoinitiators, which is assigned to the same assignee as the present invention.

BACKGROUND OF THE INVENTION

Prior to the present invention, moisture curable epoxy compositions were provided which contained dicarbonyl chelates as curing agents, as shown by Cella, U.S. Pat. No. 4,116,886, assigned to the same assignee as the present invention. As taught by Cella certain moisture sensitive dicarbonyl chelates of main row elements of Group IIIa-Va, were capable of effecting the moisture cure of epoxy resins to provide sealants, coating compounds, glues and encapsulants. As shown in the above referenced copending application of James V. Crivello, Ser. No. 949,642, certain hexafluoro metalloid phosphonium salts, such as triphenylphenacylphosphonium hexafluorophosphate and hexafluoroarsenate, can be used as photoinitiators for epoxy coating compositions resulting in the production of tack-free films in a minute or less when exposed to ultra violet light. These UV curable compositions are also shown by Crivello U.S. Pat. No. 4,069,055 also assigned to the same assignee as the present invention.

It has now been discovered that certain aryloxy phosphonium salts of the formula,

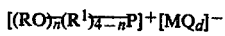  (1)

have been found useful as curing agents for epoxy resins when utilized in effective amounts to provide moisture curable cationically polymerizable coating compositions, where R and R$^1$ are monovalent aryl radicals selected from C$_{(6-13)}$ hydrocarbon radicals and radicals of the formula

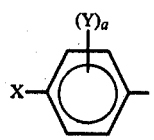

where X is selected from C$_{(1-8)}$ alkoxy, nitrile, acyloxy, halogen and nitro, Y is selected from C$_{(1-8)}$ alkyl and X radicals, M is selected from B, As, Sb and P, O is a halogen radical, a is whole number equal to 0 to 4 exclusive, d is an integer equal to 4-6 inclusive, and n is an integer equal to 1 to 4 inclusive.

STATEMENT OF THE INVENTION

The present invention relates to moisture curable cationically polymerizable organic resin compositions and aryloxyphosphonium salts utilized in such compositions.

There is provided by the present invention, moisture curable compositions which comprise, (A) a cationically polymerizable organic material and
(B) an effective amount of an aryloxyphosphonium salt of formula (1).

Radicals included within R and R$^1$ of formula (1) are, for example, phenyl, tolyl, xylyl, naphthyl, anthryl, etc., and substituted derivatives of such monovalent aryl radicals having from 1 to 4 nuclear bound radicals selected from cyano, nitro, halogen radicals such as chloro, bromo, fluoro, etc.; C$_{(1-8)}$ alkoxy radicals, such as methoxy, ethoxy, propoxy, etc.; acyloxy radicals such as carbomethoxy, carboethoxy, etc;. M is a transition metal such as antimony, iron, tin, bismuth, aluminum, gallium, indium, titanium, zirconium, vanadium, chromium, manganese, cesium, rare-earth metals, such as lanthanides, for example, cerium, etc.; actinides such as thorium, protactinium, uranium, neptunium, etc., and metalloids such as boron, phosphorus, arsenic, etc.

Included by the aryloxyphosphonium salts of formula (1) are, for example,

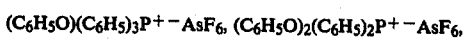

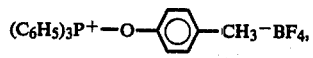

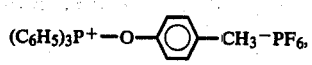

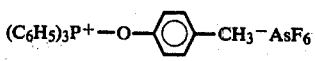

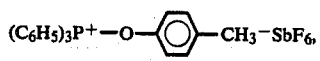

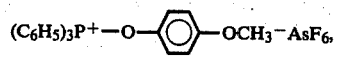

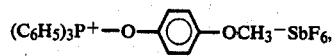

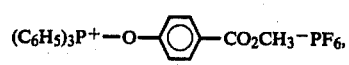

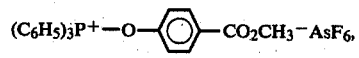

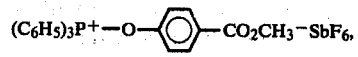

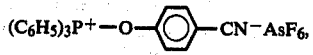

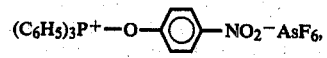

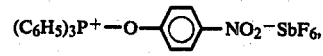

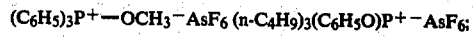

Aryloxytriphenylphosphonium halides can be utilized as precursors for some of the aryloxyphosphonium metal or metalloid halide salts included within formula (1). These precursors can be prepared by the method of L. V. Nesterov and R. I. Mutalapova, *Zh. Obshch. Khim.* 37, 1843 (1967) and G. Hilgetag, *Z. Chem.* 14, 233 (1974). A metathesis of the corresponding aryloxytriphenylphosphonium chloride with an alkali metal hexafluoro metalloid salt such as potassium hexafluoroarsenate will provide the corresponding hexafluoroarsenate salt within the scope of formula (1). In accordance with the aforementioned method of Nesterov et al, aryloxytriphenylphosphonium chlorides can be prepared from triphenylphosphine, chlorine and an appropriate phenol. In instances where it is desired to replace one of the phenyl groups of triphenylphosphine by a phenoxy group, treatment of phenyl diphenylphosphonite with chlorine followed by phenol will result in the formation of diphenyldiphenoxyphosphonium hexafluoroarsenate.

It has been found that phenols having electron withdrawing groups as substituents can provide for a preferred class of triphenylphosphonium salts as shown by the following formula,

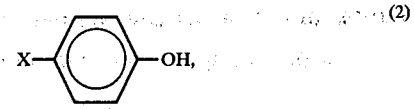

where X is defined above.

Some of the phenols included within formula (2), are, for example,

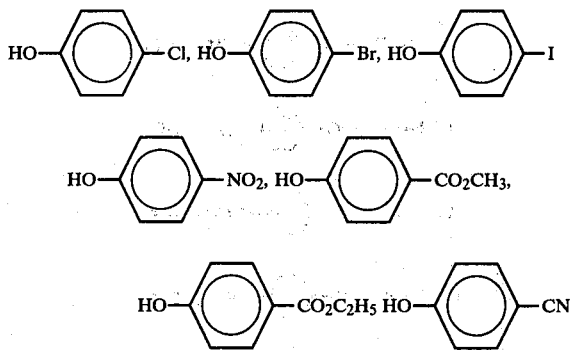

Included by the term cationically polymerizable organic material is epoxy resin which includes any monomeric, dimeric or oligomeric or polymeric epoxy material containing one or a plurality of epoxy functional groups. For example, those resins which result from the reaction of bisphenol-A (4,4'-isopropylidenediphenol) and epichlorohydrin, or by the reaction of low molecular weight phenolformaldehyde resin (Novolak resin) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl compounds or vinyl copolymers containing glycidyl acrylate or methacrylate as one of the comonomers. Other classes of epoxy containing polymers amenable to cure using the above catalysts are epoxysiloxane resins, epoxy-polyurethanes and epoxypolyesters. Such polymers usually have epoxy functional groups at the ends of their chains. Epoxy-siloxane resins and method for making are more particularly shown by E. P. Plueddemann and G. Fanger, *J. Am. Chem. Soc.* 80, 632-5 (1959). As described in the literature, epoxy resins can also be modified in a number of standard ways such as reaction with amines, carboxylic acids, thiols, phenols, alcohols, etc., as shown in U.S. Pat. Nos. 2,935,488; 3,235,620; 3,369,055; 3,379,653; 3,398,211; 3,403,119; 3,563,840; 3,567,797; 3,677,995; etc. Further coreactants which can be used with epoxy resins are hydroxy terminated flexibilizers such as hydroxy terminated polyesters, shown in the Encyclopedia of Polymer Science and Technology, Vol. 6, 1967, Interscience Publishers, New York, pp. 209–271 and particularly p. 238.

Included by the thermosetting organic condensation resins of formaldehyde which can be used in the practice of the present invention are, for example, urea type resins, phenolformaldehyde type resin.

In addition, there can be used melamine thiourea resins, melamine, or urea aldehyde resins, cresol-formaldehyde resins and combinations with other carboxy, hydroxyl, amino and mercapto containing resins, such as polyesters, alkyds and polysulfides.

A further category of the organic materials which can be used to make the polymerizable compositions are cyclic ethers which are convertible to thermoplastics. Included by such cyclic ethers are, for example, oxetanes such as 3,3-bis-chloromethyloxetane, alkoxyoxetanes as shown by Schroeter U.S. Pat. No. 3,673,216, assigned to the same assignee as the present invention; oxolanes such as tetrahydrofuran, oxepanes, oxygen containing spiro compounds, trioxane, dioxolane, etc.

In addition to cyclic ethers there are also included cyclic esters such as β-lactones, for example propiolactone, cyclic amines, such as 1,3,3-trimethyl-azetidine and organosilicon cyclics, for example, materials included by the formula,

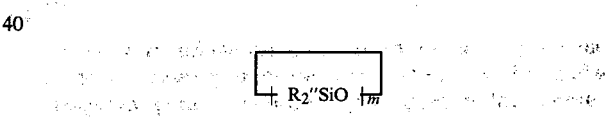

where R'' can be the same or different monovalent organic radical such as methyl or phenyl and m is an integer equal to 3 to 8 inclusive. An example of an organosilicon cyclic is hexamethyl trisiloxane, octamethyltetrasiloxane, etc. The products made in accordance with the present invention are high molecular weight oils and gums.

The moisture curable compositions of the present invention can be made by blending the cationically polymerizable organic material with at least an effective amount of the aryloxyphosphonium salt which is 0.1% to 20% by weight and preferably 1% to 5% of the aryloxyphosphonium salt based on the weight of the moisture curable composition. The resulting curable composition can be in the form of a varnish having a viscosity of from 1 to 100,000 centipoises at 25° C. or of a free flowing powder, depending upon the nature of the cationically polymerizable organic material. Moisture curable compositions can be applied to a variety of substrates by conventional means and cured to a tack-free state within 1 to 1600 minutes, depending upon the percent moisture in the atmosphere. Depending upon such factors as the nature of the cationically polymerizable organic material, percent humidity and the thickness of the applied coating, a tack-free cure can be achieved within 1 minute to 40 minutes.

Some of the applications in which the curable compositions of the present invention can be used are, for example, protective decorative, and insulating coatings, potting compounds, printing inks, sealants, adhesives, wire insulation, textile coatings, varnishes, etc.

In order that those skilled in the art will be better able to practice the invention, the following examples are given by way of illustration and not by way of limitation. All parts are by weight.

EXAMPLE 1

Chlorine gas was bubbled through a solution of triphenylphosphine (10 mmol) in 20 ml of distilled methylene chloride at 0° C. until the solution became light green. There was added to this solution (10 mmol) of phenol and the solution was stirred 2–4 hours at room temperature. A solution of potassium hexafluoroarsenate (10 mmol) in 20 ml of distilled acetone was then added. This resulted in an immediate precipitate of potassium chloride. The solution was filtered and anhydrous ether was added to the filtrate to precipitate the desired salt. Filtration resulted in a product which was recrystallized from a mixture of chloroform and diethylether. Based on method of preparation, the product was phenoxytriphenylphosphonium hexafluoroarsenate.

A series of phenols was utilized in the same procedure to produce a variety of phenoxytriphenylphosphonium salts having the following formula:

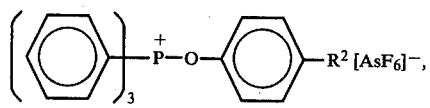

which were characterized by $^{31}P$ nmr, H nmr, IR and MP° C. The following table shows the results obtained, where $R^2$ in the above formula is shown in Table I below:

TABLE I

| $R^2$ | $^{31}P$ nmr shift[a], ppm | MP °C. | IR bands cm$^{-1}$ |
|---|---|---|---|
| —H | 65.81 | 168–188° | — |
| —CH$_3$ | 65.36 | 158.5–162° | — |
| —OCH$_3$ | 65.53 | 142–148° | — |
| —CN | 67.96 | 161–185° | 2230 |
| —CO$_2$CH$_3$ | 66.83 | 152–165° | 1720 |
| —NO$_2$ | 68.06 | 140–150° | 1530, 1350 |

[a]δ scale relative to external H$_3$PO$_4$

EXAMPLE 2

Five parts of epoxy resin were catalyzed with 3% by weight of aryloxyphosphonium salt dissolved in a small amount of methylene chloride. Three different resins were evaluated. There was utilized CY179 which is biscycloaliphatic epoxy of Ciba Geigy Company. A mixture of 60% of CY179 with 40% Epon 828, which is bisglycidyl ether of bisphenol-A of Shell Chemical Company. Gel times were measured in both air and 80% relative humidity. The term "gel time" signifies the number of minutes required to convert a thin film of the resin to the tack-free hardened state on a glass substrate. The following results were obtained where the aryloxyphosphonium salts utilized are those shown in Example 1.

TABLE II

| | Gel Time in Minutes | | | | | |
|---|---|---|---|---|---|---|
| | CY 179 | | 60% CY179-40% Epon 828 | | Epon 828 | |
| $R^2$ | Air | 80% humidity | Air | 80% humidity | Air | 80% humidity |
| —H | 120 | 40 | 1260 | 200 | >4000[a] | >4000[a] |
| —CH$_3$ | 270 | 90 | 1260 | 1260 | >4000[a] | >4000[a] |
| —OCH$_3$ | 1260 | 120 | 1560 | 1260 | >4000[a] | >4000[a] |
| —CN | [b] | [b] | 20 | 15 | 40 | 40 |
| —CO$_2$CH$_3$ | 15 | 10 | 30 | 15 | 135 | 135 |
| —NO$_2$ | 5 | 5 | 5 | 5 | 40 | 40 |

[a]>4000 implies no gellation during test period
[b]Catalyst precipitated from resin The above results show that when $R^2$ of the arylphosphonium salt of Example 1 is an electron withdrawing group, the reactivity of the aryloxytriphenylphosphonium salt is enhanced.

Although the above examples are directed to only a few of the very many variables of the present invention, it should be understood that the present invention includes a much broader class of moisture curable composition based on the use of aryloxyphosphonium salts of formula (1) and various cationically polymerizable organic materials shown in the description preceding these examples. In addition, the present invention also includes a much broader class of aryloxyphosphonium salts.

What we claim as new and desire to secure by Letters Patent of the United States is:

1. Moisture curable compositions which comprises,
   (A) a cationically polymerizable organic material and
   (B) an effective amount of an aryloxyphosphonium salt of the formula, $$[(RO)_{\overline{n}}(R^1)_{\overline{4-n}}P]^+[MQ_d]^-$$

where R and $R^1$ are monovalent aryl radicals selected from $C_{(6-13)}$ hydrocarbon radicals and radicals of the formula,

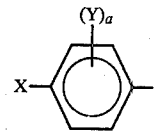

where X is selected from $C_{(1-8)}$ alkoxy, nitrile, acyloxy, halogen and nitro, Y is selected from hydrogen, $C_{(1-8)}$ alkyl and X radicals, and $C_{(6-13)}$ halogenated monovalent hydrocarbon radicals, M is selected from B, As, Sb and P, Q is a halogen radical, a is a whole number equal to 0 to 4 inclusive, d is an integer equal to 4–6 inclusive and n is an integer equal to 1 to 4 inclusive.

2. A composition in accordance with claim 1, where the cationically polymerizable material is an epoxy resin.

3. A composition in accordance with claim 1, where the cationically polymerizable material is phenol-formaldehyde.

4. A composition in accordance with claim 1, where the aryloxyphosphonium salt is diphenoxydiphenylphosphonium hexafluoroarsenate.

5. A composition in accordance with claim 1, where the aryloxyphosphonium salt is (p-carbomethoxyphenoxy)triphenylphosphonium hexafluoroarsenate.

6. A composition in accordance with claim 1, where the aryloxyphosphonium salt is (p-nitrophenoxy)triphenylphosphonium hexafluoroarsenate.

7. A composition in accordance with claim 1, where the aryloxyphosphonium salt is (p-methoxyphenoxy)triphenylphosphonium hexafluoroarsenate.

* * * * *